US000001951H

(19) United States

(12) Statutory Invention Registration (10) Reg. No.: US H1951 H

Theodoridis et al. (43) Published: Mar. 6, 2001

(54) HERBICIDAL BENZOFURANYL DERIVED URACILS AND PRODUCTION THEREOF

(76) Inventors: George Theodoridis, 9701 Mill Creek Rd., Apt. 1519, Levittown, PA (US) 19054; Scott D. Crawford, 7 Dominion Dr., Jackson, NJ (US) 08527

(21) Appl. No.: 09/469,821

(22) Filed: Dec. 22, 1999

(51) Int. Cl.[7] ..... C07D 401/00; C07D 239/02; A01N 63/00

(52) U.S. Cl. ..... 544/310; 544/314; 504/118

*Primary Examiner*—Michael J. Carone
*Assistant Examiner*—Aileen J. Baker
(74) *Attorney, Agent, or Firm*—FMC Corporation

(57) ABSTRACT

It has now been found that certain novel benzofuranyl derived uracils have provided unexpected pre-emergent and post-emergent herbicidal efficacy. These compounds are represented by formula I

I

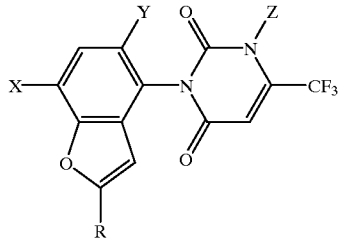

Preferred are those of formula I where R is fluoroalkyl, carboxyalkyl, alkoxycarbonylalkyl, alkoxycarbonylhaloalkyl, alkenoxycarbonylalkyl, or mono- or dialkylaminocarbonylalkyl; X is halogen; Y is hydrogen or halogen; and, Z is methyl or amino. Novel intermediates to the compounds of formula I are also disclosed.

18 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL BENZOFURANYL DERIVED URACILS AND PRODUCTION THEREOF

This invention relates generally to the field of controlling unwanted plant species in agriculture, and in particular to novel herbicidal compounds and intermediates thereto; as well as methods for the use of the herbicidal compounds and compositions thereof.

There is a continuing demand for new herbicides. Herbicides are useful for controlling unwanted vegetation i.e., weeds, which may otherwise cause significant damage to crops such as wheat, corn, soybeans and cotton, to name a few. For crop protection, so-called "selective" herbicides are desired that control the weeds without damaging the crop to any significant degree. Such crops are said to exhibit tolerance to the herbicide. In certain other situations, it is desirable to use herbicides that provide complete vegetation control such as in areas around railroad tracks and other structures. While many commercial products are available that provide selective or complete vegetation control, demand exists for new herbicides that are more effective and less costly, and meet requisite safety characteristics.

As an aid to harvesting there is also a demand for new, safe, more effective, and less costly compounds that cause defoliation and/or desiccation of cultivated plant parts. Such compounds would be useful in the harvesting of, for example, cotton, potatoes, rape, sunflowers, soybeans, and broadbeans.

SUMMARY OF THE INVENTION

It has now been found that certain novel 2-substituted-benzofuran4-yl derived uracils possess improved pre-emergent and post-emergent herbicidal activity. These compounds are represented by formula I

I

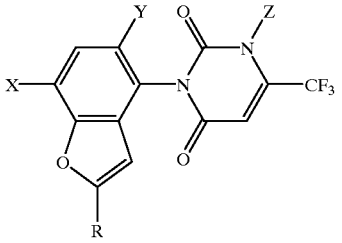

where R, X, Y, and Z are described below. Preferred are those where R is fluoroalkyl, carboxyalkyl, alkoxycarbonylalkyl, or mono- or dialkylaminocarbonylalkyl; X is chlorine; Y is fluorine, and Z is methyl or amino. Certain intermediates used to prepare these compounds are also novel and are included among the preferred embodiments of the present invention:

DEFINITIONS

The modifier "about" is used herein to indicate that certain preferred operating ranges, such as ranges for molar ratios for reactants, material amounts, and reaction times and temperatures, are not fixedly determined. The meaning will often be apparent to one of ordinary skill. For example, a recitation of a reaction time of about 18 hours in reference to, for example, the time required to complete an organic chemical reaction would be interpreted to include other like reaction times that can be expected to favor a useful completion of the reaction, such as 16 hours or 24 hours. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As used in this specification and unless otherwise indicated the term "alkyl" or "alkoxy" used alone or as part of a larger moiety includes one to six carbon atoms. The term "alkenyl" or "alkynyl", used alone or as part of a larger moiety, includes two to six carbon atoms. "Halogen" refers to fluorine, chlorine, or bromine; "TEA" refers to triethylamine; "DMF" refers to N,N-dimethylformamide; "EtOAc" refers to ethyl acetate; and "DAST" refers to diethylaminosulfur trifluoride. The term "ambient temperature" refers to a temperature range of about 20° C. to 30° C. The term "pesticides" refers to herbicides, insecticides, fungicides, or nematicides.

DETAILED DESCRIPTION OF THE INVENTION

The present invention relates to certain new and useful compounds, namely certain novel 2-substituted-benzofuran4-yl derived uracils that possess at least improved pre-emergent and post-emergent herbicidal activity. These compounds are represented by formula I

I

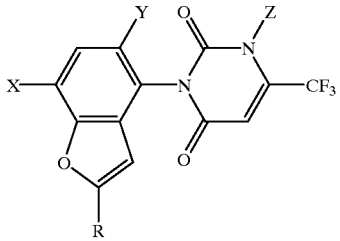

wherein

R is fluoroalkyl, hydroxyalkyl, alkoxyalkyl, cyanoalkyl, carboxyalkyl, alkylcarbonyloxyalkyl, alkoxycarbonylalkyl, alkenoxycarbonylalkyl, alkoxycarbonylhaloalkyl, alkoxycarbonylalkoxyalkyl, alkoxycarbonylaminoalkyl, aminocarbonylalkyl, aminocarbonylalkoxyalkyl, mono or dialkylaminocarbonylalkyl, alkylcarbonylaminoalkyl, aminosulfinylalkyl, alkylaminosulfonylalkyl, alkylsulfonylaminoalkyl, 1,3-dioxolan-2-ylalkyl, or 1,3-oxazolin-2-ylalkyl;

X is halogen, cyano, nitro, or trihaloalkyl;

Y is hydrogen or halogen;

Z is hydrogen, alkyl, cyanoalkyl, alkenyl, alkynyl, amino, alkoxyalkyl, or alkoxycarbonylalkyl; with the proviso that when Z is methyl or amino R is not hydroxyalkyl, alkoxyalkyl, or alkylcarbonyloxyalkyl.

Preferred species are those of formula I where R is fluoroalkyl, carboxyalkyl, alkoxycarbonylalkyl, alkoxycarbonylhaloalkyl, alkenoxycarbonylalkyl, or mono or dialkylaminocarbonylalkyl where alkyl and alkoxy as part of the larger moiety are one to three carbon atoms, and alkenoxy as part of the larger moiety is two to three carbon atoms; X is halogen; Y is hydrogen or halogen; and, Z is methyl or amino.

Particularly preferred species are those compounds of formula I where R is fluoroalkyl, carboxyalkyl, alkoxycarbonylalkyl, or mono- or dialkylaminocarbonylalkyl where alkyl and alkoxy as part of the larger moiety are one to three carbon atoms; X is chlorine; Y is fluorine, and Z is methyl or amino. Further preferred species are those compounds recited at Table 1 hereinbelow, named herein Compounds 1–47.

Another aspect of this invention relates to novel intermediates useful in the preparation of compounds of formula I. These compounds are represented by formula 1

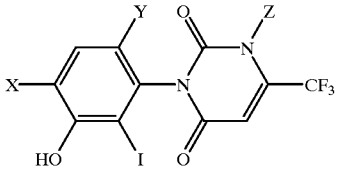

1 wherein;

X is halogen, cyano, nitro, or trihaloalkyl;

Y is hydrogen or halogen;

Z is hydrogen, alkyl, cyanoalkyl, alkenyl, alkynyl, amino, alkoxyalkyl, or alkoxycarbonylalkyl.

Of particular use as intermediates are those compounds of formula 1 wherein X is chlorine; Y is fluorine, and Z is hydrogen, methyl or amino.

The benzofuranyl-derived uracils of the present invention (formula I) can be synthesized by methods that individually are known to one skilled in the art. Scheme 1 below illustrates a general procedure for synthesizing compounds of the present invention where R is fluoroalkyl, hydroxyalkyl, carboxyalkyl, alkoxycarbonylalkyl, or mono- or dialkylaminocarbonylalkyl.

Scheme 1

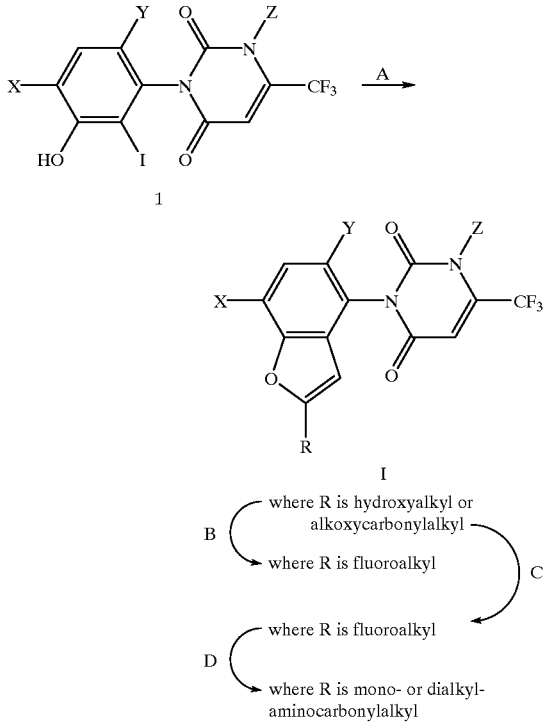

(A) HC≡CH—R, $Pd(Ph_3P)_2Cl_2$, CuI, TEA, DMF (B) DAST, $CH_2Cl_2$ (C) $BBr_3$, $CH_2Cl_2$ (D) mono- or dialkylamine-HCl, $C_6H_7ClN^+I^-$, TEA, $CH_2Cl_2$ The novel 6-iodo intermediate 1, is preferably prepared by the reaction of a 3-(2,4-optionally substituted-5-hydroxyphenyl)-1-methyl-6-trifluoromethyl-2,4(1 H,3H)-pyrimidinedione with silver trifluoroacetate and elemental iodine, as set forth in U.S. Pat. No. 5,602,077. The reactions of 1 with appropriately substituted acetylenes according to step (A) afford in one step a number of the targeted benzofuranyl-substituted uracils I of the present invention. Some of the so-prepared uracils I are further reacted, yielding additional targeted compounds. For example, I, where R is hydroxyalkyl may be halogenated, affording derivatives I where R is haloalkyl. In a preferred method, according to step (B); the reaction of I with, for example, DAST in a suitable aprotic solvent (selected from, but not limited to, heptane, dioxane, toluene, diethyl ether, carbon tetrachloride, chloroform, methylene chloride, acetone, acetonitrile, EtOAc, DMF, or dimethyl sulfoxide; preferably methylene chloride), affords I where R is fluoroalkyl. Dealkylation of I where R is alkoxycarbonylalkyl in a suitable aprotic solvent, according to step (C), affords I where R is carboxyalkyl; which may in turn, according to step (D), be reacted further under mildly basic conditions conferred by, for example, TEA or the like, with a mono- or dialkylamine hydrochloride, in the presence of a suitable coupling reagent in an aprotic solvent to give I where R is mono- or dialkylaminocarbonylalkyl. A suitable coupling reagent functions to activate the carboxyalkyl moiety towards nucleophilic attack, thus aiding the formation of the mono- or dialkylaminocarbonylalkyl derivative. Other useful coupling reagents are, for example, 1,1-carbonyidiimidazole, dicyclohexylcarbodiimide and other diimides.

The present invention also relates to herbicidal compositions that combine herbicidally effective amounts of the active compounds with adjuvants and carriers normally employed in the art for facilitating the dispersion of active ingredients for the particular utility desired. One skilled in the art will of course recognize that the formulation and mode of application of a toxicant may affect the activity of the material in a given application. Thus, for agricultural use the present herbicidal compounds may be formulated as a granular of relatively large particle size (for example, without limitation, 8/16 or 4/8 US Mesh), as water-soluble or water-dispersible granules, as powdery dusts, as wettable powders, as emulsifiable concentrates, as solutions, or as any of other known types of agriculturally-useful formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as about 0.1%, about 0.2% or about 0.5% to as much as about 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing about 1.0 part or less of the herbicidal compound and about 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains about 80.0 parts of the herbicidal compound, about 18 parts of Palmetto clay, and about 1 part of sodium lignosulfonate and about 0.3 part of sulfonated aliphatic polyester as wetting agents. Additional wetting agent and/or oil will frequently be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises from about 0.5 to about 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of from about 0.5 to about 95%, frequently from about 10 to about 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise from about 1 to about 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier, such as the Freon fluorinated hydrocarbons, may also be used. Water-soluble or waterd-ispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, and the like, may be diluted with water to give a concentration of active ingredient in the range of from about 0.1% to about 2%.

In one embodiment, the active herbicidal compounds of this invention are formulated and/or applied with one or more second compounds. Second compounds include, but are not limited to, other pesticides, plant growth regulators, fertilizers, soil conditioners, or other agricultural chemicals. The active herbicidal compounds of this invention may also be used as effective soil sterilants as well as selective herbicides in agriculture. In applying an active compound of this invention, whether formulated alone or with other agricultural chemicals, an effective amount and concentration of the active compound is of course employed; the amount may be as low as, for example, from about 1 to about 250 g/ha, preferably from about 4 to about 30 gha. For field use, where there are losses of herbicide, higher application rates (e.g., four times the rates mentioned above) may be employed.

When the active herbicidal compounds of the present invention are used in combination with one or more of second compounds, e.g., with other pesticides such as herbicides, the other herbicides preferably include, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/–)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro4-methyl4-(1 -methylethyl)-5-oxo-1 H-imidazol-2-yl]-3-pyridine-carboxylic acid ("imazapyr"), a reaction product comprising (+/–)-2-[4,5-dihydro4-methyl4-(1 -methylethyl)-5-oxo-1 H-imidazol-2-yl]-4-methylbenzoic acid and (+/–)2-[4,5-dihydro4-methyl4-(1-methylethyl)-5-oxo-1H-imidazol-2-yl]-5-methylbenzoic acid ("imazamethabenz"), (+/–)-2-[4,5-dihydro4-methyl-4-(1-methylethyl)-5-oxo-1H-imidazol-2-yl]-5-ethyl-3-pyridinecarboxylic acid ("imazethapyr"), and (+/–)-2-[4,5-dihydro4-methyl4-(1-methylethyl)-5-oxo-1H-imidazol-2-yl]-3-quinolinecarboxylic acid ("imazaquin"); diphenyl ethers such as 5-[2-chloro4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]suffonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]amino]sulfonyl]-1 -methy-1H-pyrazol4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benzenesulfonamide ("triasulfuron"); 2-(4-aryloxyphenoxy)alkanoic acids such as (+/–)-2 [4-[(6-chloro-2-benzoxazolyl)oxy]phenoxy]propanoic acid (fenoxaprop"), (+/−)-2-[4 [[5-(trifluoromethyl)-2-pyridinyl] oxy]phenoxy]propanoic acid ("fluazifop"), (+/−)-2-[4-(6chloro-2-quinoxalinyl)oxy]phenoxy]propanoic acid ("quizalofop"), and (+/−-)-2-[(2,4-dichlorophenoxy) phenoxy]propanoic acid ("diclofop"); benzothiadiazinones such as 3-(1 -methylethyl)-1H-2,1,3-benzothiadiazin-4(3H)-one-2,2-dioxide ("bentazone"); 2-chloroacetanilides such as N-(butoxymethyl)-2-chloro-N-(2,6-diethylphenyl) acetamide ("butachlor"), 2-chloro-N-(2-ethyl-6-methylphenyl)-N-(2-methoxy-1 -methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl) acetamide ("dimethenamide"); arenecarboxylic acids such as 3,6-dichloro-2-methoxybenzoic acid ("dicamba"); and pyridyloxyacetic acids such as [(4-amino-3,5-dichloro-6-fluoro-2-pyridinyl)oxy]acetic acid ("fluroxypyr").

When the active herbicidal compounds of the present invention are used in combination with one or more of second compounds, e.g., with other pesticides such as insecticides, the insecticides preferably include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, biphenthrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, and imidacioprid.

When the active herbicidal compounds of the present invention are used in combination with one or more of second compounds, e.g., with other pesticides such as fungicides, the fungicides preferably include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; and inorganic fungicides, such as copper and sulphur products.

When the active herbicidal compounds of the present invention are used in combination with one or more of second compounds, e.g., with other pesticides such as nematicides, the nematicides preferably include, for example: carbofuran, carbosulfan, turbufos, aldecarb, ethoprop, fenamphos, oxamyl, isazofos, and cadusafos.

When the active herbicidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, and trinexapac-ethyl.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation . When the active herbicidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, bacillus, pseudomonas, azotobacter, azospitillum, rhizobium, and soil-borne cyanobacteria.

Fertilizers are plant food supplements which commonly contain nitrogen, phosphorus, and potassium. When the active herbicidal compounds of the present invention are used in combination with one or more of second compounds, e.g., with other materials such as fertilizers, the fertilizers preferably include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate.

The following examples further illustrate the present invention, but, of course, should not be construed as in any way limiting its scope. The examples are organized to present protocols for the synthesis of the benzofuranyl-derived compounds of the present invention, set forth a list of such synthesized species, and set forth certain biological data indicating the efficacy of such compounds.

EXAMPLE 1

This example illustrates a method for the synthesis of 3-[7-chloro-5-fluoro4-(1-methyl-6-trifluoromethyl-2,4(1H,3H)-pyrimidinedion-3-yl)benzofuran-2-yl]propanoic acid (Compound 16).

Step A Prepare 3-(4-chloro-2-fluoro-5-hydroxy-6-iodophenyl)-1-methyl-6-tnifluoromethyl-2,4(1H,3H)-pyrimidinedione Under a nitrogen atmosphere, a solution of 6.5 grams (0.019 mole) of 3-(4-chloro-2-fluoro-5-hydroxyphenyl)-1-methyl-6-trifluoromethyl-2,4(1H,3H)-pyrimidinedione and 5.0 grams (0.022 mole) of silver trifluoroacetate in 100 mL of methylene chloride was stirred, and 5.3 grams (0.021 mole) of iodine in 100 mL of methylene chloride was added dropwise. Upon completion of addition, the reaction mixture was stirred at ambient temperature for about 24 hours. After this time the reaction mixture was filtered through diatomaceous earth. The filtrate was then washed with an aqueous solution of 10% sodium bisulfite. The organic layer was washed with an aqueous saturated sodium chloride solution and dried with sodium sulfate. The mixture was filtered and the filtrate was concentrated under reduced pressure to a residual oil. The oil was purified by column chromatography on silica gel, yielding 4.2 grams of subject compound. The NMR spectrum was consistent with the proposed structure.

Step B Prepare methyl 3-[7-chloro-5-fluoro-4-(1-methyl-6-trifluoromethyl-2,4(1H,3H)-pyrimidinedion-3-yl) benzofuran-2-yl]propanoate Under a nitrogen atmosphere, a solution of 2.2 grams (0.0047 mole) of 3-(4-chloro-2-fluoro-5-hydroxy-6-iodophenyl)-1-methyl-6-trifluoromethyl-2,4(1H,3H)-pyrimidinedione, 1.1 grams (0.0095 mole) of methyl 4-pentynoate, and 2.6 mL (0.0190 mole) of TEA in 60 mL of DMF was stirred, and 0.2 gram (0.0002 mole) of bis (triphenylphosphine)palladium(II) chloride, followed by 0.09 gram (0.0005 mole) of copper(I) chloride were added. Upon completion of addition, the reaction mixture was stirred for 30 minutes at ambient temperature, then it was warmed to 70° C. where it stirred for about 16 hours. The reaction mixture was cooled to ambient temperature, poured into cold aqueous 3N hydrochloric acid, and extracted repeatedly with EtOAc. The combined extracts were washed with an aqueous saturated sodium chloride solution and dried with sodium sulfate. The mixture was filtered, and the filtrate was concentrated under reduced pressure to a residual oil. The oil was purified by column chromatography on silica gel, yielding 1.7 grams of subject compound. The NMR spectrum was consistent with the proposed structure.

Step C Prepare Compound 16

Under a nitrogen atmosphere, a stirred solution of 1.7 grams (0.0037 mole) of methyl 3-[7-chloro-5-fluoro4-(1-methyl-6-trifluoromethyl-2,4(1H,3H)-pyrimidinedion-3-yl) benzofuran-2-yl]propanoate in 70 mL of methylene chloride was cooled to −40° C., and 14.7 mL (1.0M in methylene chloride) of boron tribromide was added dropwise during a 15 minute period. Upon completion of addition, the reaction mixture was allowed to warm to ambient temperature as it stirred for about 20 hours. After this time the reaction mixture was poured into water, then extracted repeatedly with methylene chloride. The combined extracts were washed with aqueous saturated solutions of sodium bicarbonate and sodium chloride; then dried with sodium sulfate. The mixture was filtered and concentrated under reduced pressure, yielding a small amount of residue which NMR analysis indicated was intended reaction product. The sodium bicarbonate wash was acidified to pH 2 with concentrated hydrochloric acid and extracted with EtOAc. The EtOAc solution was washed with an aqueous saturated solution of sodium chloride, then dried with sodium sulfate. The mixture was filtered and concentrated under reduced pressure, yielding another residue which NMR analysis indicated was intended reaction product. The two crops of product were combined and dissolved in diethyl ether. The resulting solution was washed repeatedly with an aqueous saturated solution of sodium bicarbonate. The bicarbonate washes were combined and extracted repeatedly with EtOAc. The combined EtOAc extracts were then washed with an aqueous saturated solution of sodium chloride and dried with sodium sulfate. The mixture was filtered and concentrated under reduced pressure, yielding 0.9 gram of subject compound; mp 102–104° C. The NMR spectrum was consistent with the proposed structure.

EXAMPLE 2

This example illustrated a method for the synthesis of N,N-dimethyl-3-[7-chloro-5-fluoro-4-(1-methyl-6-trifluoromethyl-2,4(1H,3H)-pyrimidinedion-3-yl) benzofuran-2-yl]propanamide (Compound 24).

Under a nitrogen atmosphere, a solution 0.70 gram (0.0016 mole) of Compound 16, 0.50 gram (0.0019 mole) of 2-chloro-1-methylpyridinium iodide, and 0.13 gram (0.0016 mole) of dimethylamine hydrochloride in 10 mL of methylene chloride was stirred, and 0.76 mL (0.0054 mole) of TEA was added. Upon completion of addition, the reaction mixture was warmed to reflux where it stirred for about 2.5 hours. The reaction mixture was then cooled to ambient temperature and poured into cool water. The mixture was repeatedly extracted with methylene chloride. The combined extracts were washed with an with an aqueous saturated solution of sodium chloride, then dried with sodium sulfate. The mixture was filtered and concentrated under reduced pressure to a residual oil. The oil was purified by column chromatography on silica gel, yielding 0.42 gram of subject compound; mp 55–58° C. The NMR spectrum was consistent with the proposed structure.

EXAMPLE 3

This example illustrated a method for the synthesis of [7-chloro-5-fluoro-4-(1-methyl-6-tnifluoromethyl-2,4(1H,3H)-pyrimidinedion-3-yl)benzofuran-2-yl]methyl fluoride (Compound 4).

Step A Prepare [7-chloro-5-fluoro-4-(1-methyl-6-trifluoromethyl-2,4(1H,3H)-pyrimidinedion-3-yl) benzofuran-2-yl]methanol This compound was prepared in the manner of Step B of Example 1; using 3.0 grams (0.007 mole) of 3-(4-chloro-2-fluoro-5-hydroxy-6-iodophenyl)-1-methyl-6-trifluoromethyl-2,4(1H,3H)-pyrimidinedione, 0.8 mL (0.013 mole) of 2-propyn-1-ol, 0.23 gram (0.0003 mole) of bis (triphenylphosphine)palladium(II) chloride, 0.12 gram (0.0007 mole) of copper(I) chloride, and 3.6 mL (0.026 mole) of TEA in 50 mL of DMF. The yield of subject compound was 1.1 grams. The NMR spectrum was consistent with the proposed structure.

Step B Prepare Compound 4

Under a nitrogen atmosphere, a stirred solution of 0.5 gram (0.0013 mole) of [7-chloro-5-fluoro4-(1-methyl-6-trifluoromethyl-2,4(1H,3H)-pyrimidinedion-3-yl) benzofuran-2-yl]methanol in 15 mL of methylene chloride was cooled to 0° C., and 0.42 mL (0.0032 mole) of diethylaminosulfur trifluoride was added dropwise. Upon completion of addition, the reaction mixture was stirred at ambient temperature for four hours. The reaction mixture was then poured into cold water and repeatedly extracted with methylene chloride. The combined extracts were dried with sodium sulfate and filtered. The filtrate was concentrated under reduced pressure to an oil residue. The oil was purified by column chromatography on silica gel, yielding 0.2 gram of subject compound; mp 139–141° C. The NMR spectrum was consistent with the proposed structure.

EXAMPLE 4

This example sets forth representative compounds of the present invention, each synthesized in accordance with the methods of Examples 1–3, as follows:

TABLE 1

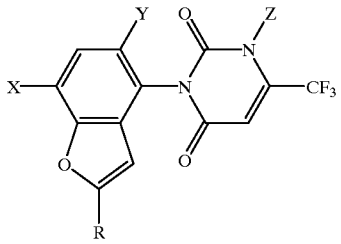

| Cmpd No. | X | Y | Z | R |
|---|---|---|---|---|
| 1 | Cl | H | $CH_3$ | $(CH_2)_2F$ |
| 2 | Cl | H | $CH_3$ | $(CH_2)_2CO_2H$ |
| 3 | Cl | Cl | $CH_3$ | $(CH_2)_2CO_2H$ |
| 4 | Cl | F | $CH_3$ | $CH_2F$ |
| 5 | Cl | F | $CH_3$ | $(CH_2)_2F$ |
| 6 | Cl | F | $CH_3$ | $CH_2CH(CH_3)F$ |
| 7 | Cl | F | $CH_3$ | $CH_2C(CH_3)_2F$ |
| 8 | Cl | F | $CH_3$ | $(CH_2)_2OH$ |
| 9 | Cl | F | $CH_3$ | $CH_2C(CH_3)_2OH$ |
| 10 | Cl | F | $CH_3$ | $(CH_2)_2OCH_3$ |
| 11 | Cl | F | $CH_3$ | $(CH_2)_2OC(O)CH_3$ |
| 12 | Cl | F | $CH_3$ | $C(CH_3)_2OCH(CH_3)CO_2CH_3$ |
| 13 | Cl | F | $CH_3$ | $C(CH_3)_2OCH_2C(O)NH_2$ |
| 14 | Cl | F | $CH_3$ | $(CH_2)_3CN$ |
| 15 | Cl | F | H | $(CH_2)_2CO_2H$ |
| 16 | Cl | F | $CH_3$ | $(CH_2)_2CO_2H$ |
| 17 | Cl | F | $CH_3$ | $(CH_2)_2CO_2C_2H_5$ |
| 18 | Cl | F | $CH_3$ | $CH_2CH(Cl)CO_2C_2H_5$ |
| 19 | Cl | F | $CH_3$ | $CH_2CH(CH_3)CO_2C_2H_5$ |
| 20 | Cl | F | $CH_3$ | $(CH_2)_2CO_2CH(CH_3)_2$ |
| 21 | Cl | F | $CH_3$ | $(CH_2)_2CO_2CH_2CH{=}CH_2$ |
| 22 | Cl | F | $CH_3$ | $(CH_2)_2C(O)NH_2$ |
| 23 | Cl | F | $CH_3$ | $(CH_2)_2C(O)NHCH_3$ |
| 24 | Cl | F | $CH_3$ | $(CH_2)_2C(O)N(CH_3)_2$ |
| 25 | Cl | F | $CH_3$ | $(CH_2)_2NHC(O)CH_3$ |
| 26 | Cl | F | $CH_3$ | $(CH_2)_2NHCO_2CH_3$ |
| 27 | Cl | F | $CH_3$ | $(CH_2)_2NHSO_2CH_3$ |
| 28 | Cl | F | $CH_3$ | $(CH_2)_2SONH_2$ |
| 29 | Cl | F | $CH_3$ | $(CH_2)_2SO_2NHCH_3$ |
| 30 | Cl | F | $CH_3$ | 2-(1,3-dioxolan-2-yl)ethyl |
| 31 | Cl | F | $CH_3$ | 2-(1,3-oxazolin-2-yl)ethyl |
| 32 | Cl | F | $C_2H_5$ | $(CH_2)_2CO_2H$ |
| 33 | Cl | F | n-$C_3H_7$ | $(CH_2)_2CO_2H$ |
| 34 | Cl | F | $CH(CH_3)_2$ | $(CH_2)_2CO_2H$ |
| 35 | Cl | F | $CH_2CN$ | $(CH_2)_2CO_2H$ |
| 36 | Cl | F | $CH_2CH{=}CH_2$ | $(CH_2)_2CO_2H$ |
| 37 | Cl | F | $CH_2OCH_3$ | $(CH_2)_2CO_2H$ |
| 38 | Cl | F | $CH_2CO_2C_2H_5$ | $(CH_2)_2CO_2H$ |
| 39 | Cl | F | $CH_2C{\equiv}CH_2$ | $(CH_2)_2CO_2H$ |
| 40 | CN | F | $CH_3$ | $(CH_2)_2CO_2H$ |
| 41 | $NO_2$ | F | $CH_3$ | $(CH_2)_2CO_2H$ |
| 42 | $CF_3$ | F | $CH_3$ | $(CH_2)_2CO_2H$ |
| 43 | Cl | F | $NH_2$ | $(CH_2)_2F$ |
| 44 | Cl | F | $NH_2$ | $(CH_2)_2)OH$ |
| 45 | Cl | H | $NH_2$ | $(CH_2)_2CO_2H$ |
| 46 | Cl | F | $NH_2$ | $(CH_2)_2CO_2H$ |
| 47 | Cl | F | $NH_2$ | $(CH_2)_2CO_2C_2H_5$ |

Melting point determinations were conducted using standard procedures for Compounds 4, 5, 8, 14, 16, 17, and 24, providing the following data:

TABLE 2

| Cmpd No | Melting Point (° C.) | Cmpd No | Melting Point (° C.) | Cmpd No | Melting Point (° C.) |
|---|---|---|---|---|---|
| 4 | 139–141 | 5 | 65–67 | 8 | 86–88 |
| 14 | 139–141 | 16 | 102–104 | 17 | 39–41 |
| 24 | 55–58 | | | | |

EXAMPLE 5

This example sets forth representative intermediates useful in the preparation of compounds of the present invention, each synthesized in accordance with the methods of Examples 1–3, as follows:

TABLE 3

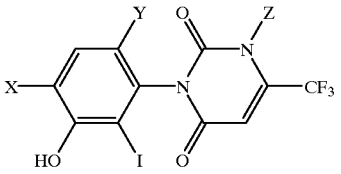

| Cmpd No. | X | Y | Z |
|---|---|---|---|
| 1a | Cl | H | H |
| 2a | Cl | Cl | H |
| 3a | Cl | F | H |
| 4a | CN | F | H |
| 5a | $NO_2$ | F | H |
| 6a | $CF_3$ | F | H |
| 7a | Cl | H | $CH_3$ |
| 8a | Cl | Cl | $CH_3$ |
| 9a | Cl | F | $CH_3$ |
| 10a | $CF_3$ | F | $CH_3$ |
| 11a | Cl | H | $NH_2$ |
| 12a | Cl | Cl | $NH_2$ |
| 13a | Cl | F | $NH_2$ |
| 14a | $CF_3$ | F | $NH_2$ |
| 15a | Cl | F | $C_2H_5$ |
| 16a | Cl | F | n-$C_3H_7$ |
| 17a | Cl | F | $CH(CH_3)_2$ |
| 18a | Cl | F | $CH_2CN$ |
| 19a | Cl | F | $CH_2CH{=}CH_2$ |
| 20a | Cl | F | $CH_2OCH_3$ |
| 21a | Cl | F | $CH_2CO_2C_2H_5$ |
| 22a | Cl | F | $CH_2C{\equiv}CH_2$ |

EXAMPLE 6

This example sets forth biological testing conducted on certain benzofuranyl-derived uracils of the present invention.

The benzofuranyl-derived uracils of this invention were tested for pre- and postemergence herbicidal activity using a variety of crops and weeds. The test plants include, but are not limited to, soybean (Glycine max_var. Winchester), field corn (*Zea mays* var. Pioneer 3732), wheat (*Triticum aestivum* var. Lew), morningglory (*Ipomea lacunosa* or *Ipomea hederacea*), velvetleaf (*Abutilon theophrasti*, green foxtail (*Setaria viridis*), Johnsongrass (*Sorghum halepense*), blackgrass (*Aloepecurus myosuroides*), common chickweed (*Stellaria media*), and common cocklebur (*Xanthium strumanum* L.).

In the postemergence test, seeds of the plant species named above were planted in flats containing the appropriate soil mixture where they were maintained to allow the seeds to germinate. When the plants in these flats reached the proper stage of growth, flats for the preemergence tests were planted in a like manner. The flats containing the postemergence and preemergence test plant species were then sprayed with an appropriately concentrated water/acetone solution of test compound. Once treated the flats were maintained, along with untreated controls, for about fourteen days. All treated plants were then examined for phytotoxicity, which was expressed as percent control where 0 is no effect and 100 is complete control. Effective rates of application for the compounds of the present invention range from 0.001 to 3 kg/ha of active compound, more likely from 0.003 to 1 Kg/ha.

Herbicidal activity data at selected application rates are given for various compounds of this invention in Tables 4 and 5. The test compounds are identified by numbers which correspond to those in Table 1.

TABLE 4

PREEMERGENCE HERBICIDAL ACTIVITY (% CONTROL)

| Cmpd. No. | SOY | WHT | CRN | ABUTH | IPOSS | STEME | XANPE | ALOMY | SETVI | SORHA |
|---|---|---|---|---|---|---|---|---|---|---|
| 4 | 80 | 65 | 80 | 100 | 90 | 100 | 90 | 75 | 100 | ND |
| 5 | 100 | 90 | 95 | 100 | 100 | 100 | 100 | 95 | 100 | 95 |
| 8 | 80 | 75 | 90 | 100 | 100 | 80 | 100 | 70 | 100 | ND |
| 14 | 100 | 60 | 90 | 100 | 80 | 100 | 60 | 90 | 100 | 90 |
| 16 | 100 | 70 | 60 | 100 | 100 | 100 | 100 | 90 | 100 | 100 |
| 17 | 100 | 70 | 50 | 100 | 100 | 80 | 100 | 60 | 100 | ND |
| 24 | 100 | 95 | 90 | 100 | 100 | 100 | 100 | 80 | 100 | 100 |

TABLE 5

POSTEMERGENCE HERBICIDAL ACTIVITY (% CONTROL)

| Cmpd. No. | SOY | WHT | CRN | ABUTH | IPOSS | STEME | XANPE | ALOMY | SETVI | SORHA |
|---|---|---|---|---|---|---|---|---|---|---|
| 4 | 100 | 70 | 85 | 100 | 100 | 100 | 100 | 70 | 100 | ND |
| 5 | 100 | 100 | 95 | 100 | 100 | ND | 100 | 100 | 100 | 100 |
| 8 | 95 | 60 | 80 | 100 | 100 | 100 | 100 | 60 | 100 | 95 |
| 14 | 90 | 100 | 90 | 100 | 100 | ND | 100 | 95 | 80 | 100 |
| 16 | 100 | 100 | 85 | 100 | 100 | 100 | 100 | 90 | 100 | 90 |
| 17 | 100 | 100 | 95 | 100 | 100 | 100 | 100 | 80 | 100 | 100 |
| 24 | 100 | 80 | 80 | 100 | 100 | 90 | 100 | 75 | 70 | 75 |

Rate of Application is 0.10 kg/Ha
SOY is soybean, WHT is wheat, CRN is corn, ABUTH is velvetleaf, IPOSS is morningglory, STEMME is chickweed, XANPE is cocklebur, ALOMY is blackgrass, SETVI is green foxtail, and SORHA is johnsongrass
ND is no data While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

We claim:

1. A compound of the formula:

I

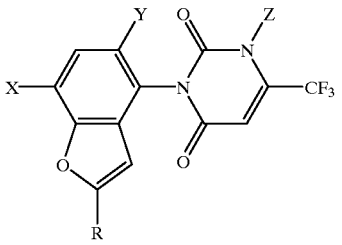

wherein

R is fluoroalkyl, hydroxyalkyl, alkoxyalkyl, cyanoalkyl, carboxyalkyl, alkylcarbonyloxyalkyl, alkoxycarbonylalkyl, alkenoxycarbonylalkyl, alkoxycarbonylhaloalkyl, alkoxycarbonylalkoxyalkyl, alkoxycarbonylaminoalkyl, aminocarbonylalkyl, aminocarbonylalkoxyalkyl, mono or dialkylaminocarbonylalkyl, alkylcarbonylaminoalkyl, aminosulfinylalkyl, alkylaminosulfonylalkyl, alkylsulfonylaminoalkyl, 1,3-dioxolan-2-ylalkyl, or 1,3-oxazolin-2-ylalkyl;

X is halogen, cyano, nitro, or trihaloalkyl;

Y is hydrogen or halogen;

Z is hydrogen, alkyl, cyanoalkyl, alkenyl, alkynyl, amino, alkoxyalkyl, or alkoxycarbonylalkyl; with the proviso that when Z is methyl or amino R is not hydroxyalkyl, alkoxyalkyl, or alkylcarbonyloxyalkyl.

2. The compound according to claim 1 where R is fluoroalkyl, carboxyalkyl, alkoxycarbonylalkyl, alkoxycarbonylhaloalkyl, alkenoxycarbonylalkyl, or mono- or dialkylaminocarbonylalkyl where alkyl and alkoxy as part of the larger moiety are one to three carbon atoms and alkenoxy as part of the larger moiety is two to three carbon atoms; X is halogen; Y is hydrogen or halogen; and, Z is methyl or amino.

3. The compound according to claim 1 where R is fluoroalkyl, carboxyalkyl, alkoxycarbonylalkyl, or mono- or dialkylaminocarbonylalkyl where alkyl and alkoxy as part of the larger moiety are one to three carbon atoms; X is chlorine; Y is fluorine, and Z is methyl or amino.

4. The compound of claim 1, which is selected from the group consisting of compounds 1–47 of Table 1.

5. A compound of the formula:

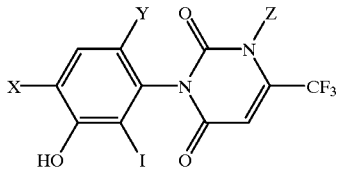

wherein;

X is halogen, cyano, nitro, or trihaloalkyl;

Y is hydrogen or halogen;

Z is hydrogen, alkyl, cyanoalkyl, alkenyl, alkynyl, amino, alkoxyalkyl, or alkoxycarbonylalkyl.

6. The compound according to claim 5 where X is chlorine; Y is fluorine, and Z is hydrogen, methyl or amino.

7. An herbicidal composition comprising an herbicidally effective amount of a compound of claim 1, and an herbicidally compatible carrier.

8. The herbicidal composition of claim 7, further comprising one or more second compounds.

9. A method of controlling undesired plant growth, comprising applying an herbicidally effective amount of a composition of claim 7 to a locus where undesired plants are growing or are expected to grow.

10. An herbicidal composition comprising an herbicidally effective amount of a compound of claim 2, and an herbicidally compatible carrier.

11. The herbicidal composition of claim 10, further comprising one or more second compounds.

12. A method of controlling undesired plant growth, comprising applying an herbicidally effective amount of a composition of claim 10 to a locus where undesired plants are growing or are expected to grow.

13. An herbicidal composition comprising an herbicidally effective amount of a compound of claim 3, and an herbicidally compatible carrier.

14. The herbicidal composition of claim 13, further comprising on or more second compounds.

15. A method of controlling undesired plant growth, comprising applying an herbicidally effective amount of a composition of claim 13 to a locus where undesired plants are growing or are expected to grow.

16. An herbicidal composition comprising an herbicidally effective amount of a compound of claim 4, and an herbicidally compatible carrier.

17. The herbicidal composition of claim 16, further comprising on or more second compounds.

18. A method of controlling undesired plant growth, comprising applying an herbicidally effective amount of a composition of claim 16 to a locus where undesired plants are growing or are expected to grow.

* * * * *